United States Patent [19]

Buhl et al.

[11] Patent Number: 4,971,912
[45] Date of Patent: Nov. 20, 1990

[54] APPARATUS AND METHOD FOR THE SEPARATION OF IMMISCIBLE LIQUIDS

[75] Inventors: Steven N. Buhl, Chappaqua; Syed I. Ahmad, Orangeburg; Arden Grassick, Cold Spring, all of N.Y.

[73] Assignee: Technicon Instruments Corporation, Tarrytown, N.Y.

[21] Appl. No.: 73,050

[22] Filed: Jul. 14, 1987

[51] Int. Cl.$^5$ ............................................. G01N 35/08
[52] U.S. Cl. ................................ 436/52; 210/500.36; 210/506; 210/510.1; 422/58; 422/81; 422/82; 427/387; 436/53; 436/169; 436/170
[58] Field of Search .................... 422/81, 82, 56–58; 436/52, 53, 169, 170; 210/500.36, 506, 510.1; 427/387

[56] References Cited

U.S. PATENT DOCUMENTS

| | | | |
|---|---|---|---|
| 2,960,462 | 11/1960 | Lee et al. | 210/500.36 |
| 3,260,413 | 7/1966 | Natelson | 422/66 |
| 3,479,141 | 11/1969 | Smythe et al. | 422/82 X |
| 3,661,460 | 5/1972 | Elking et al. | 250/222.2 |
| 3,949,121 | 4/1976 | Kenney | 427/98 |
| 4,121,466 | 10/1978 | Reichler et al. | 73/864.22 |
| 4,210,697 | 7/1980 | Adiletta | 427/244 |
| 4,253,846 | 3/1981 | Smythe et al. | 436/53 |
| 4,266,559 | 5/1981 | Akhavi | 73/664.11 X |
| 4,357,301 | 11/1982 | Cassaday et al. | 422/64 |
| 4,418,039 | 11/1983 | Adler | 422/82 |
| 4,668,472 | 5/1987 | Sakamoto et al. | 422/58 |

Primary Examiner—Robert J. Hill, Jr.
Attorney, Agent, or Firm—Jeffrey M. Greenman; James J. Romano, Jr.

[57] ABSTRACT

Apparatus and method for the separation of immiscible liquids are provided, and comprise the use of separator means having a surface which is preferentially "wettable" by one of the liquids to the substantial exclusion of another of the liquids. In use, the liquids are flowed from a common liquid source onto said surface with the one liquid being sorbed thereby to the substantial exclusion of the other liquid to thus substantially separate the liquids. The separator means surface may be maintained essentially level to retain the substantially separated liquid thereon, or may be inclined to result in the flow of the same therefrom under the influence of the force of gravity. Alternatively, the separator means may be made of a liquid-permeable material to permit the flow of the substantially separated liquid therethrough and therefrom under the influence of the force of gravity. The apparatus and method are particularly adapted to the substantial separation of aqueous sample liquids from hydrophobic isolation liquids which encapsulate the same; and are readily combinable with a sample liquid reaction device to effectively combine the sample liquid separation and reaction operations. The material of the separator means may be inherently hydrophobic, or may be rendered super-hydrophobic by the surface coating thereof with a super-hydrophobic coating material.

21 Claims, 8 Drawing Sheets

FIG. 17
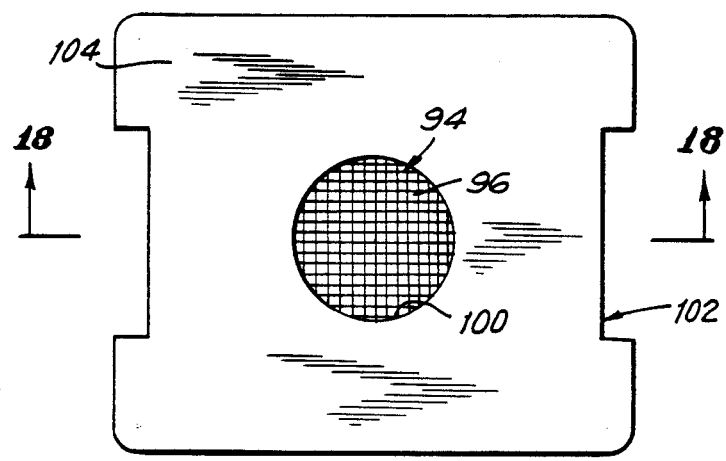
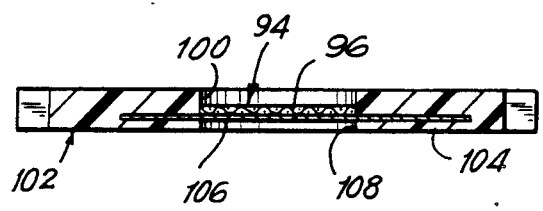
FIG. 18

APPARATUS AND METHOD FOR THE SEPARATION OF IMMISCIBLE LIQUIDS

BACKGROUND OF THE INVENTION

1. Field of the Invention.

This invention relates to new and improved apparatus and method for the virtually immediate and substantially complete separation of immiscible liquids; which are particularly adapted to such separation of sample liquids from immiscible isolation liquids within which the sample liquids are encapsulated for minimization of sample liquid carryover attendant automated sample liquid analysis.

2. Description of the Prior Art.

Although a number of apparatus and methods are known for the substantial separation of sample liquids from immiscible isolation liquids within which the same are encapsulated for minimization of sample liquid carryover attendant sample liquid analysis, these will generally be found to rely primarily upon the natural separational effects of the differences in specific gravity between those liquids, and are thus not effective to accomplish the virtually immediate, and complete in terms of totally different locations of the thusly substantially separated liquids, separation of the liquids as are inherently provided by the apparatus and method of this invention.

More specifically, U.S. Pat. No. 4,121,466 issued Oct. 24, 1978 to Allen Reickler, et al, for "Liquid Dispenser With An Improved Probe" and assigned to the assignee her discloses the use of an immiscible hydrophobic isolation liquid to encapsulate successive aqueous sample liquids for minimization of sample liquid carryover attendant sample liquid analysis. In this apparatus, wherein the isolation liquid is of greater density than the sample liquids, the former is simply allowed to settle out from the latter to the bottom of a reaction receptacle into which the isolation liquid-encapsulated sample liquids are dispensed, thereby leaving the sample liquid readily accessible for reaction with reagent liquids as may then be introduced into the receptacle. This settling out of the isolation liquid can and does take time and, in any event, leaves the thusly separated isolation and sample liquids in essentially the same location, e.g. the reaction receptacle.

In like manner, U.S. Pat. No. 4,357,301 issued Nov. 2, 1982 to Michael M. Cassaday, et al for "Reaction Cuvette" and assigned to the assignee hereof, also discloses the use of an immiscible isolation liquid to encapsulate successive aqueous sample liquids for minimization of sample liquid carryover attendant sample liquid analysis. In this apparatus wherein the isolation liquid is again hydrophobic and apparently of greater density than the sample liquids, sharp projections or the like of a hydrophilic material are provided at the bottom of the reaction cuvette, and operate to puncture the isolation liquid-encapsulated sample liquids as the same are introduced into the cuvette; thereby freeing for reaction the sample liquids from the isolation liquid which essentially sinks to the bottom of the cuvette. Again, this separation can and does take time and, in any event, leaves the isolation liquid and sample liquids in the location, e.g. the reaction cuvette and, of course, in substantial surface contact at the isolation liquid-sample liquid interface.

Under the above circumstances, it has been determined by applicants that the continued presence of the "separated" isolation liquid with the sample liquid at essentially the same location, and with substantial surface contact therebetween at the isolation liquid-sample liquid interface, can and does present significant problems with regard to the accuracy of subsequent sample liquid analysis results; and especially in those instances wherein those sample liquid analysis results are arrived at through use of sample liquid analysis methodologies involving, for example, reflectance spectroscopy or ion selective electrodes, colorimetry, cell counting and/or enzyme coil operation.

Hydrophobic filtration, for example as disclosed by the "non-wet" filter of U.S. Pat. No. 4,266,559 issued May 12, 1981 to David S. Akhavi for "Blood Sampler," wherein a filter of hydrophobic material is used to prevent the escape of an aqueous sample liquid from a collection device while permitting the passage of air therethrough to enable filling of the device, is also known in the prior art; but is not seen as relevant to the separation of immiscible liquids as disclosed herein.

Also of limited relevance to immiscible liquid separation are conventional debubbler devices which have now become standard in continuous flow sample liquid analysis systems and which operate to remove the air segments from a continuously flowing, air segmented sample liquid stream prior to sample liquid analysis. These debubbler devices, which operate primarily on the very significant differences in specific gravity between air and sample liquids are clearly totally irrelevant to the separation of immiscible liquids as disclosed herein.

No relevant prior art is, in any event, known to applicants with regard to the combination of immiscible sample and isolation liquid separational and sample liquid reaction devices to effectively combine those functions in the manner made possible by the apparatus and method of this invention.

OBJECTS OF THE INVENTION

It is, accordingly, and object of our invention to provide new and improved apparatus and method for the separation of immiscible liquids.

It is another object of our invention to provide apparatus and method as above which are operable to effect the virtually immediate separation of such liquids.

It is another object of our invention to provide apparatus and method as above which are operable to separate said liquids to distinct and spaced locations without contact therebetween.

It is another object of our invention to provide apparatus and method as above which are of particularly simple and straightforward configuration and manner of operation.

It is another object of our invention to provide apparatus as above which have no moving parts.

It is another object of our invention to provide apparatus as above which require the use of only readily available, relatively inexpensive materials of proven effectiveness for the task at hand, and minimal if any modification of those materials, in the fabrication thereof.

It is another object of our invention to provide apparatus as above which may be fabricated at low cost.

It is another object of our invention to provide apparatus as above which are disposable in economically feasible manner after but a single use.

It is another object of our invention to provide apparatus and method as above which are particularly adapted to the separation of immiscible liquids wherein one of said liquids is substantially encapsulated in the other of said liquids.

It is another object of our invention to provide apparatus and method as above which are particularly adapted to the separation of immiscible liquids wherein one of said liquids is an aqueous liquid.

It is another object of our invention to provide apparatus and method as above which are particularly adapted to the separation of immiscible liquids wherein one of said liquids is a sample liquid which is to be subsequently analyzed.

It is a another object of our invention to provide apparatus and method as above which are particularly adapted to the separation of immiscible liquids wherein one of said liquids is a sample liquid which is to be subsequently analyzed, and the other of said liquids is an isolation liquid which has been utilized with said sample liquid to minimize sample liquid carryover attendant the supply and processing for analysis of successive sample liquids.

It is a further object of our invention to provide apparatus and method as above for utilization in combination with a sample liquid reaction device to effectively combine the sample liquid separation and reaction operations.

SUMMARY OF THE INVENTION

As disclosed herein, the new and improved apparatus and method of our invention are embodied in immiscible liquid separation means comprising a liquid separator piece of a material including a surface which is effective to preferentially attract and sorb a first of the immiscible liquids to the substantial exclusion of a second of said liquids. The separator piece is arranged relative to a common source of said immiscible liquids to dispose the surface below the liquid source and in essential vertical alignment therewith, thereby enabling the liquids to be dropped onto the surface from the common liquids source. As the immiscible liquids come into contact with the separator piece surface, the first liquid is preferentially attracted to and sorbed by the surface to the substantial exclusion of the second liquid to thereby substantially separate the liquids. The separator piece surface may be maintained essentially level for retention of the substantially separated second liquid thereon, or may be inclined for the flow of the same therefrom under the influence of the force of gravity. As another alternative, the material of the separator piece may be permeable by the substantially separated second liquid for the flow of the same therethrough and therefrom under the influence of the force of gravity.

The separator piece takes the form of a strip of the material, or a flexible roll of the same; and, in the latter instance, means are provided to unwind the roll to progressively expose different surface portions of the material roll to the first and second immiscible liquids. For use with second liquids which are constituted by aqueous liquids, the first liquid is hydrophobic, and the separator piece surface is either hydrophobic and provided by the material of the separator piece, or super-hydrophobic and provided by a coating on the separator piece.

The apparatus and method of the invention are particularly adapted for use attendant the analysis of successive aqueous sample liquids. For such use, the first liquid is a hydrophobic isolation liquid which substantially encapsulates the successive sample liquids to minimize carryover therebetween, while the thusly encapsulated sample liquids are the second liquid. Substantial separation of the isolation and sample liquids is dictated in such instance by the fact that the isolation liquid-encapsulated sample liquids cannot, as such, be analyzed with the requisite high degree of sample liquid analysis accuracy.

Combination of the apparatus and method of the invention with a sample liquid reaction device operates to effectively combine the sample liquid separation and reaction operations in a single device through use of a permeable liquid separator piece and disposition of a sample liquid reaction element directly thereunder.

BRIEF DESCRIPTION OF THE DRAWINGS

The above and other objects and significant advantages of our invention are believed made clear by the following detailed description thereof taken in conjunction with the accompanying drawings wherein:

FIG. 17 is a top view of another application of the apparatus of our invention, there in combination with a sample liquid reactive device, to the separation of immiscible liquids; and FIG. 18 is a cross-sectional view taken essentially along line 18—18 in FIG. 17.

DETAILED DESCRIPTION OF THE INVENTION

Figure 1:
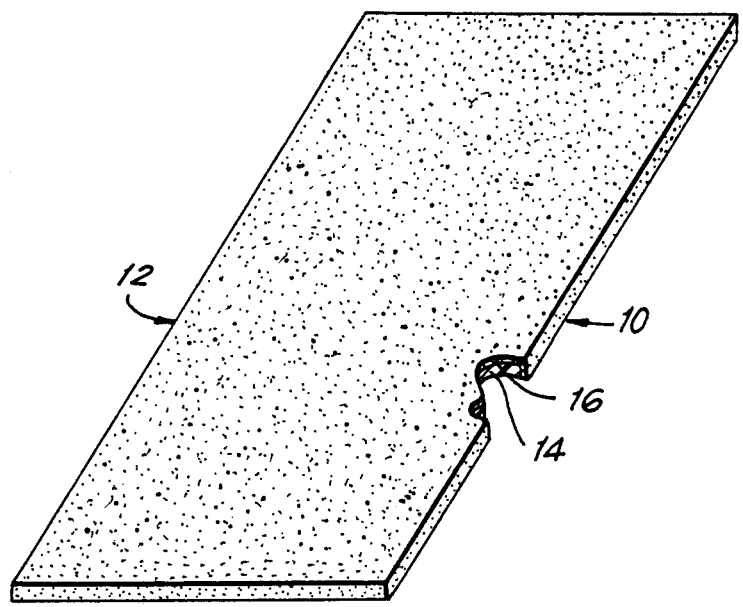
FIG. 1 is a perspective view, with part broken away, of a first embodiment of apparatus representatively configured and operable in accordance with the teachings of our invention.

Referring now to FIG. 1 of the patent application drawings, a first embodiment of new and improved, immiscible liquid separation device representatively configured and operable in accordance with the teachings of the apparatus and method of our invention is indicated generally at 10.

Separation device 10 is constituted by liquid separation means which comprise a separator piece 12 taking the form of a generally rectangular strip 14 of any suitable, readily available material. This material may, for example, be Mylar or aluminum which are not highly hydrophobic; or may be a highly hydrophobic material, for example Teflon, which may or may not be porous.

The separator piece strip 14 is thoroughly surface-coated as indicated at 16 by a super-hydrophobic coating material in the nature, for example, of Vellox Hydrophobic Coating as manufactured by M-Chem Corporation, 9 Bishop Road, Ayer, Md. 01432.

Super-hydrophobic coating materials of this nature may be understood to be effective, when applied as a surface-coating to a substrate, to very substantially increase the contact angle of a drop of aqueous liquid disposed thereon—and thus the hydrophobicity of the substrate—to a value well beyond the perpendicular. For example, such surface-coating increases the aqueous liquid drop-substrate surface contact angle from approximately 94° to approximately 127° for Teflon, and from approximately 46° to approximately 150° for aluminum.

This feature of super-hydrophobicity as exhibited by Vellox Hydrophobic Coating, and the manners in which this coating material may be readily and thoroughly applied to substrate materials of the nature here under discussion, are described in some detail in undated Technological Data Sheet as published by M-Chem Corp. and entitled "Vellox 14." As briefly described for purposes of this disclosure, super-hydrophobic coating material application generally involves the surface cleaning as required of the relevant surface area of the substrate, the application as by spraying of an appropriate clear lacquer-type primer to the thusly cleaned substrate surface area and, after a suitable drying period, the thorough application, again as by spraying, of the Vellox coating material thereover.

In addition to being intensely hydrophobic, super-hydrophobic coating materials of the nature here under discussion are known to be selectively "wettable" by a wide range of fluorinated or perfluorinated hydrocarbon, or silicone, liquids, to the substantial exclusion of aqueous liquids which are immiscible therewith; and this phenomenon of selective "wettability" of hydrophobic materials by these liquids to the substantial exclusion of immiscible aqueous liquids is discussed in some detail in U.S. Pat. No. 3,479,141 issued Nov. 18, 1969 to William J. Smythe, et al, for "Method And Apparatus For Analysis" and assigned to the assignee hereof, the disclosure of which is hereby incorporated by reference in this specification.

U.S. Pat. No. 3,479,141 also discloses the use of this concept of selective "wettability" of hydrophobic materials to minimize sample liquid carryover, e.g. the contamination of a succeeding aqueous sample liquid by the residue of a preceding aqueous sample liquid, attendant automated, successive aqueous sample liquid analysis. In accordance with that patent disclosure, this is accomplished by the encapsulation within an immiscible silicone liquid of the successive aqueous sample liquids of a continuously flowing stream thereof as the same progresses through a fluorinated hydrocarbon tubing length; with the silicone liquid functioning as an isolation liquid to isolate the aqueous sample liquids, one from the other, to prevent contact and cross-contamination therebetween, and functioning as an isolation liquid to selectively "wet" the inner tubing length wall to the substantial exclusion of the aqueous sample liquids thereby isolating the aqueous sample liquids from that tubing length inner wall and preventing a preceding aqueous sample liquid from contacting the same and leaving a residue thereon for pick-up by and contamination of a succeeding aqueous sample liquid.

Other United States Patents which relevantly disclose the application of this concept of selective "wettability" of the hydrophobic materials by isolation liquids to the substantial exclusion of immiscible aqueous sample liquids for the minimization of sample liquid carryover attendant automated, successive aqueous sample liquid analyses are U.S. Pat. No. 4,253,846 issued Mar. 3, 1981 to William J. Smythe, et al, for "Method And Apparatus For Automated Analysis of Fluid Samples" and assigned to the assignee hereof, and U.S. Pat. Nos. 4,121,466 and 4,357,301 as referred to hereinabove under the "Description of the prior art;" and the disclosures of each of these United States Patents are also incorporated by reference in this specification.

Figure 2:
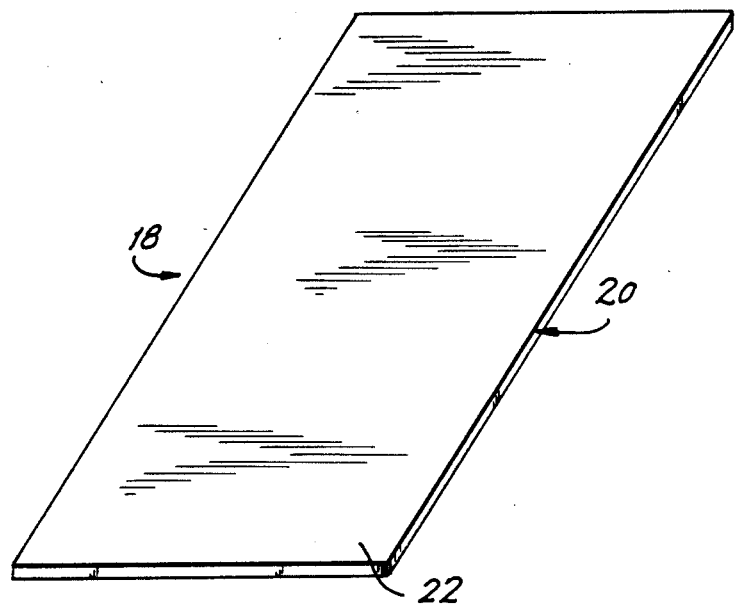
FIG. 2 is a perspective view of a second embodiment of apparatus representatively configured and operable in accordance with the teachings of our invention.

A second embodiment of new and improved immiscible liquid separation device representatively configured and operable in accordance with the teachings of the apparatus and method of our invention is indicated generally at 18 in FIG. 2. Separation device 18 is constituted by separation means which comprise an uncoated separator piece 20 taking the form of a generally rectangular strip 22 of any suitable, readily available material which is inherently highly hydrophobic, for example Teflon, which may or may not be porous. Under these circumstances, it will be immediately clear to those skilled in this art that the hydrophobicity of the uncoated separation device 18 of the embodiment of FIG. 2 in terms of the contact angle which will be established relative thereto by a drop of an aqueous liquid will not be as high as that of the super-hydrophobic material-coated separation device 10 of the embodiment of FIG. 1. The cost, however, of the separation device 18, both in terms of materials, and in terms of device fabrication, will, in most instances, be lower than the cost of the separation device 10.

Figure 3:
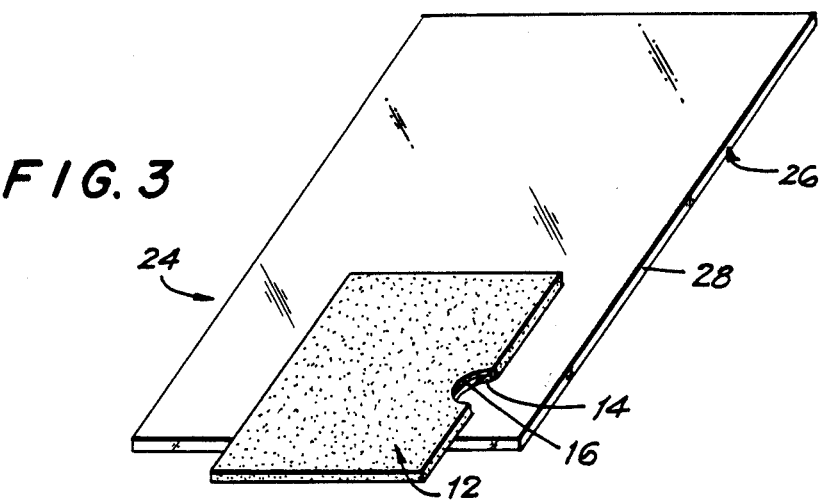
FIG. 3 is a perspective view, with part broken away, of a third embodiment of apparatus representatively configured and operable in accordance with the teachings of our invention.

A third embodiment of new and improved immiscible liquid separation device representatively configured and operable in accordance with the teachings of the apparatus and method of our invention is indicated generally at 24 in FIG. 3. In this embodiment, the liquid separation device 24, which is illustrated as comprising the super-hydrophobic material-coated separator piece 12 of the embodiment of FIG. 1, further comprises device locating and handling means as indicated generally at 26 in FIG. 3. Handling and locating means 26 take the form of a generally rectangular, standard laboratory glass slide as indicated at 28; and the separator piece 12 is fixedly secured thereto in any suitable manner, for example by an appropriate adhesive, to the upper surface of the glass slide 28 to overlie the lower edge thereof as shown. As a result, handling and location of the separation device 24 without requirement for surface-contact with the separator piece 12, is rendered particularly convenient. Alternatively, the separation device 24 of the embodiment of FIG. 3 can take the form of the uncoated, inherently highly hydrophobic separator piece 20 of the embodiment of FIG. 2.

Figure 4:
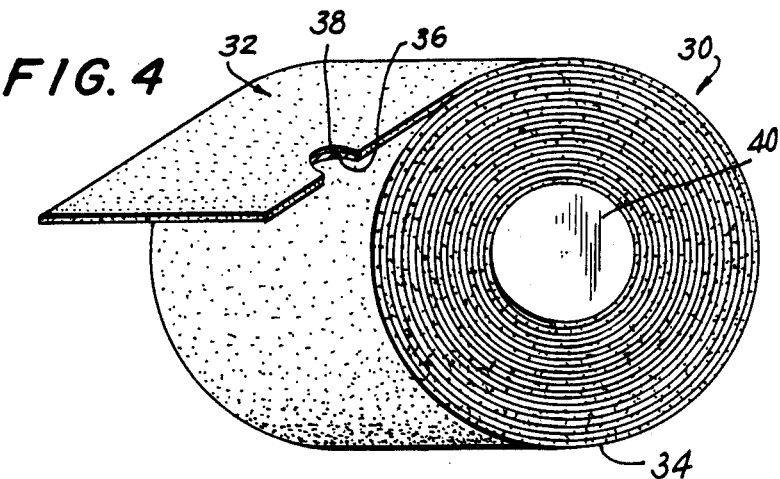
FIG. 4 is a perspective view, with part broken away, of a fourth embodiment of apparatus representatively configured and operable in accordance with the teachings of our invention.

A fourth embodiment of new and improved immiscible liquid separation device representatively configured and operable in accordance with the teachings of the apparatus and method of our invention is indicated generally at 30 in FIG. 4. In this embodiment, the liquid separator piece as there indicated at 32 is in the form of a roll 34 of any suitable, readily available flexible strip material 36, again for example Mylar, aluminum, or Teflon which may or may be not be porous, which is thoroughly surface-coated as indicated at 38 with a super-hydrophobic coating material such as Vellox in the manner described in detail hereinabove for the separator piece 12 of the embodiment of FIG. 1. Alternatively, the separator piece roll 34 can be formed from an uncoated, inherently hydrophobic material in the manner of the uncoated separator piece 20 of the embodiment of FIG. 2. Roll 34 is wound around a central spool as indicated at 40.

Figure 5:
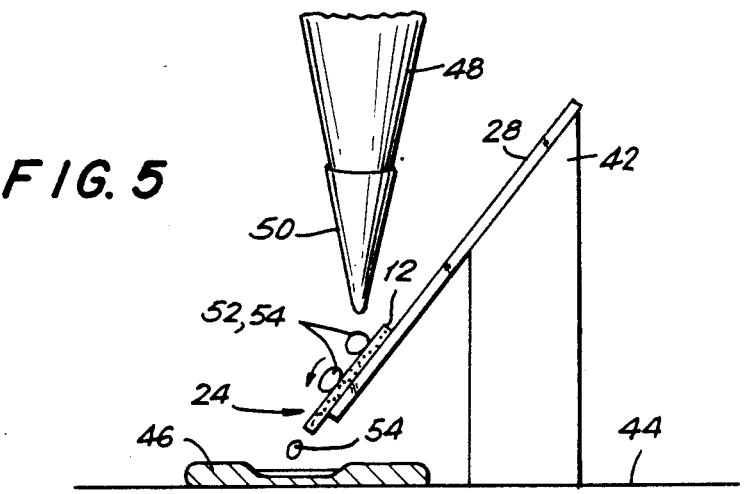
FIG. 5 is a side elevational view illustrating a first application of the apparatus and method of our invention to the separation of immiscible liquids.
Figure 6:
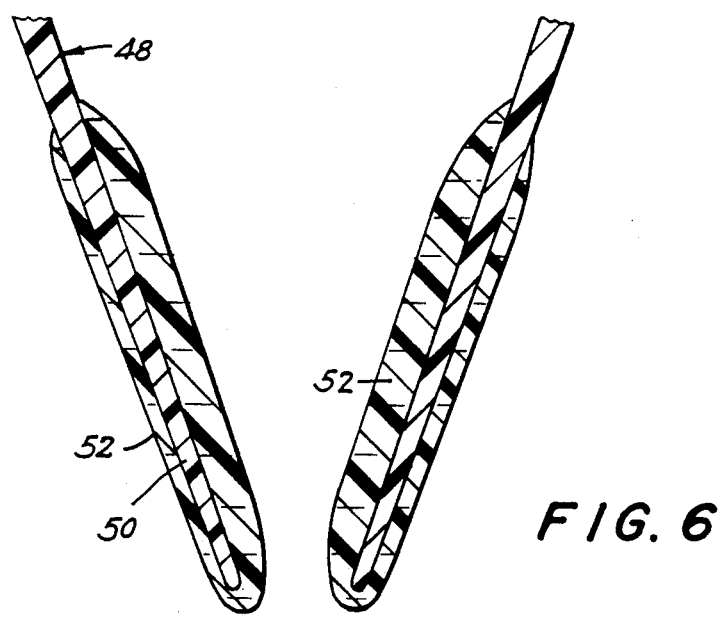
FIGS. 6 and 7 are essentially vertical cross-sectional views taken through the liquids dispensing device of FIG. 5 and illustrating the operation thereof.
Figure 7:
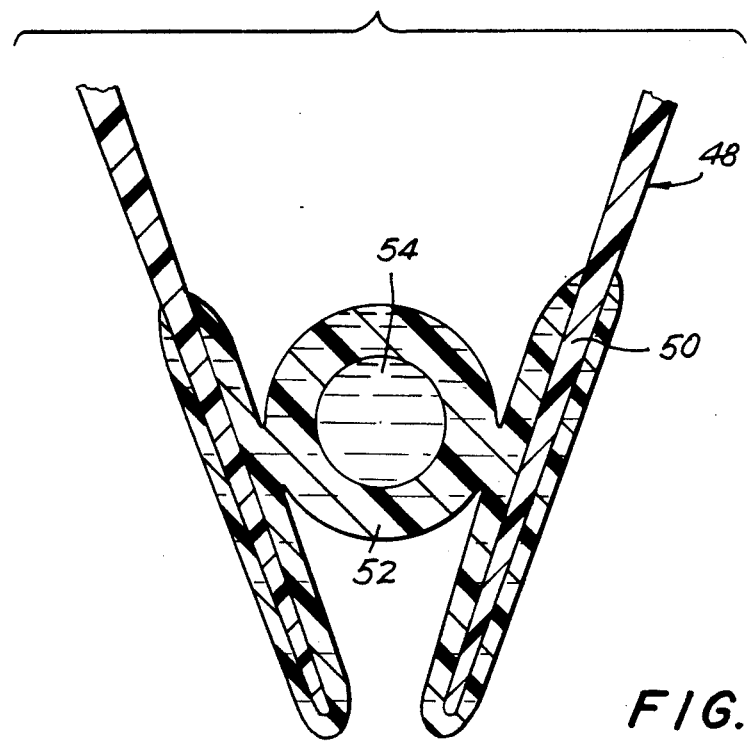

A first representative application of the new and improved immiscible liquid separation apparatus and method of our invention to that effect is illustrated in FIGS. 5, 6 and 7. In this application, which may for example be directed to the separation of an aqueous blood serum sample liquid from an immiscible isolation liquid of the nature discussed hereinabove which will selectively "wet" a hydrophobic material to the substantial exclusion of that aqueous sample liquid, and the subsequent analysis of the thusly separated blood serum sample liquid with regard to a specified constituent thereof, for example glucose, the liquid separation device 24 of the embodiment of FIG. 3 is employed; and is retained and supported in the manner of an inclined ramp in any appropriate manner by support means 42 to form an angle of, for example, 60-75° with the horizontal as represented by support surface 44.

A dry chemistry slide, for example the Fuji Glucose Dry Chem 1000 Slide as manufactured by Fuji Photo Film Co. of Asakashi-Saitamaken, 351, Japan, is indicated at 46 and may be disposed at the sample application position of a Fuji Dry Chem 1000 Analyzer. FIG. 5 makes clear that the center of slide 46 is inessential vertical alignment with the lower edge of separator piece 12.

Although essential dimensions and distances may, of course, vary in accordance with the application to which the apparatus and method of our invention are put, it may be noted that for the application of FIG. 5, a dimension of 1 cm×2 cm for the separator piece 12, the extension thereof about 2 mm beyond the lower edge of the glass laboratory slide 28, and the disposition of the lower edge of the separator piece 12 a distance of 5-10 mm above the center of slide 46, have respectively proven satisfactory.

A standard, 20 ul laboratory Pipettman is indicated at 48 in FIGS. 6 and 7, and comprises a tip 50 of an appropriately hydrophobic material, for example Teflon.

For blood sample serum analysis as described, the tip 50 of Pipettman 48 is initially dipped in a container (not shown) of the isolation liquid to result in the "wetting" of the lower portion thereof thereof with a layer of the isolation liquid as indicated at 52 in FIG. 6. The Pipettman tip 50 is then transferred to a container (not shown) of the blood sample serum liquid of interest; and a small quantity, for example 10 ul of the same aspirated thereinto. This results in a globule of the blood serum sample liquid as indicated at 54 in FIG. 7 being encapsulated and retained within the isolation liquid layer 52 in the Pipettmen tip 50; primarily as a result of the selective "wetting" of the hydrophobic material of the tip by the isolation liquid to the substantial exclusion of the aqueous blood sample serum liquid.

The Pipettman 48 is then transferred to the position thereof relative to the separation device 24 as depicted in FIG. 5 and wherein the tip 50 is in essential vertical alignment with the upper portion of the inclined separator piece 12 and, for example, disposed a distance of 5–10 mm thereabove. The isolation liquid-encapsulated blood serum sample liquid globule 54 is then released from the Pipettman 48 to fall freely onto the super-hydrophobic surface of the separator piece 12 and cascade down the same as illustrated under the influence of the force of gravity. As this occurs, the isolation liquid 52 is strongly attracted to, spread across and sorbed by the super-hydrophobic separator piece surface to selectively "wet" the same to the substantial exclusion of the aqueous blood serum sample liquid 54; while the latter is strongly repelled by the super-hydrophobic separator piece surface and falls freely off the end of the inclined separator piece 12 as illustrated onto the slide 46. Thus, substantially complete separation of the aqueous blood serum sample liquid 54 from the isolation liquid 52 is readily and effectively accomplished; and slide 46 may immediately be advanced to the non-illustrated analyzer for automatic analysis of the substantially isolation liquid-free blood serum sample liquid 54 without adverse isolation liquid-caused degradation in the accuracy of the analysis results. Although the extent of isolation liquid-caused degradation in the accuracy of blood sample liquid analysis results varies widely in accordance with the particular blood sample liquid constituent of interest, and the particular methodology utilized to quantify the same, it has been determined that, for glucose, errors in analysis accuracy in the magnitude of over 15% low can and do occur when it is attempted to analyze the blood serum sample liquid by conventional reflectance spectroscopy analysis means without first completely separating the same as described from the isolation liquid.

The above-described process may then be repeated as described for successive blood sample serum liquids of interest, without sample liquid carryover of consequence due to the fact that each of the sample liquids is substantially prevented by the isolation liquid layer 52 from contacting the wall of the Pipettman tip 50 and adhering thereto for contamination of a succeeding sample liquid, until separator piece 12 has been essentially saturated by the isolation liquid to the extent that it can no longer effectively separate the entirety of the same as described from the blood sample serum liquid globule 54 of interest. As and when this is determined to have occurred, it is, of course, a simple matter to replace the separation device 24 with a fresh one for continuation of the blood serum sample liquid analysis process.

Clearly, the separation device 10 of FIG. 1 or the separation device 18 of FIG. 2 could be utilized instead of the separation device 24 in the arrangement of FIG. 5. In such instances, the separator pieces could readily be of substantially greater dimension, for example 2 cm×8 cm to substantially increase the isolation liquid adsorption capacity thereof, and thus the number of isolation liquid-encapsulated aqueous sample liquids as could be effectively separated thereby as described; although these increases would be counteracted with regard to the separation device 18 of FIG. 2 by the fact that the same is not coated with a super-hydrophobic coating material.

Figure 8:
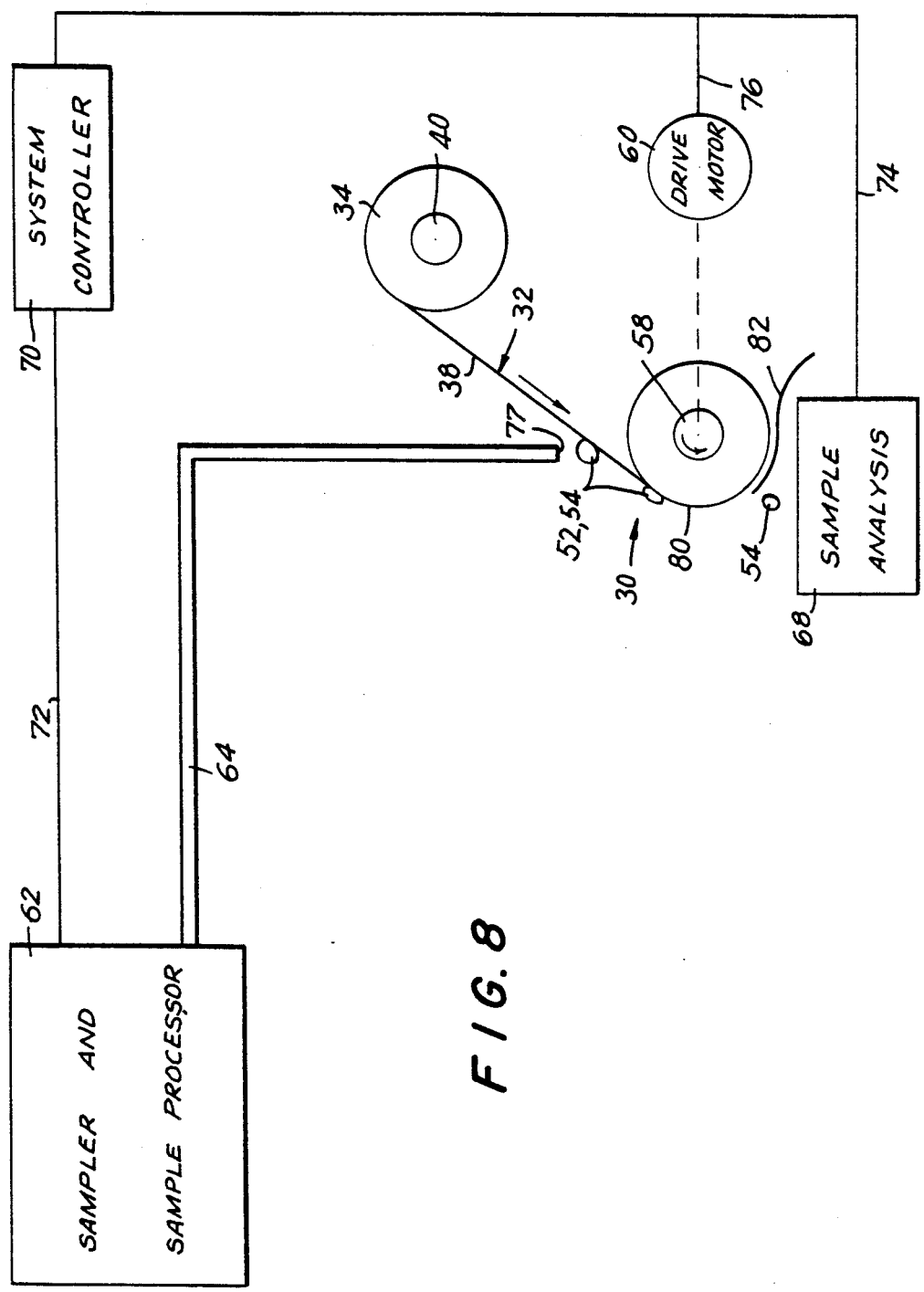
FIG. 8 is a side elevational view, with certain components depicted schematically, illustrating a second application of the apparatus and method of our invention to the separation of immiscible liquids.
Figure 9:
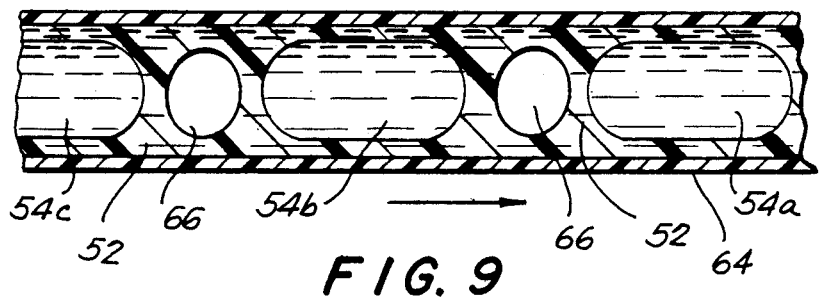
FIG. 9 is an essentially vertical cross-sectional view taken through the liquids supply conduit of FIG. 8.

A second representative application of the new and improved immiscible liquid separation apparatus and method of our invention to that effect is illustrated in FIGS. 8 and 9. In this application, which may for example be directed to the separation of successive isolation liquid-encapsulated blood serum sample liquids from a continuously flowing stream thereof—wherein the isolation liquid is immiscible with the blood serum sample liquids and selectively "wets" a hydrophobic material to the substantial exclusion thereof—and the subsequent successive analyses of the thusly separated blood serum sample liquids with regard to a particular constituent thereof, for example sodium or potassium through use of ion specific electrode analysis methodology, the liquid separation device 30 of FIG. 4 is employed, and further includes a take-up spool 58 which is spaced as shown from separation device supply spool 40, and which is operable upon the driven rotation thereof to unwind and advance the flexible separator piece 32 from the supply spool 40. To this effect, an electric drive motor as schematically indicated at 60 is provided; and the drive motor is mechanically connected as indicated to the take-up spool 58 for advancement of the flexible separator piece 22 at a rate proportional to the speed of rotation of the drive motor 60.

Sampler and sample processing means are indicated schematically at 62 in FIG. 8; and may, for example, take the general form of those disclosed in U.S. Pat. No. 4,121,466 wherein the same are operable to generate a stream of isolation liquid-encapsulated successive aqueous blood serum sample liquids in a hydrophobic conduit as indicated at 64, thereby minimizing carryover between those aqueous sample liquids and significantly increasing the accuracy of the sample liquid analysis results. This isolation liquid-encapsulated sample liquid stream is illustrated in FIG. 9 wherein the successive blood serum sample liquid segments are indicated at 54a, 54b and 54c, the isolation liquid is indicated at 52, and air-segments which operate to further minimize sample liquid carryover are indicated at 66.

Sample analysis means are indicated schematically at 68 in FIG. 8, and are operable in manner well understood by those skilled in this art to automatically analyze the blood serum sample liquids as successively supplied thereto with regard to a particular constituent thereof, in this instance sodium or potassium as described hereinabove.

A system controller is indicated schematically at 70 in FIG. 8; and may, for example, take the form of an appropriately programmed microprocessor device. Controller 70 is electrically connected as indicated by lines 72, 74 and 76 to each of sampler and sample processing means 62, sample analysis means 68 and drive motor 60 to control and synchronize the respective operations thereof.

With the outlet end 77 of the sample liquid supply conduit 64 disposed as shown in FIG. 8 slightly above and in essential vertical alignment with the center of the lower portion of the exposed length of the flexible separator piece 32 as extends between supply spool 40 and take-up spool 58, it will be clear that as each isolation liquid-encapsulated aqueous blood serum sample liquid segment 54 is flowed in turn from the conduit outlet end 77, the same will fall freely therefrom onto the super-hydrophobic surface of the separator piece 32 and cascade down the same as illustrated under the force of gravity. As this occurs, the isolation liquid 52 is strongly attracted to, spread across and sorbed by the super-hydrophobic separator piece surface to selectively "wet" the same to the substantial exclusion of the aqueous blood serum sample liquid segment 54; while the latter is strongly repelled by that super-hydrophobic separator piece surface and falls freely off of the effective "edge" thereof as indicated at 80 into the sample liquid analysis means 68 for analysis as described. Thus, substantially complete separation of the aqueous blood serum sample liquid segments 54 from the isolation liquid 52 is readily and effectively accomplished; and meaningful degradation thereby in the accuracy of the ion selective electrode blood serum sample liquids analysis results effectively prevented.

Shield means are schematically indicated at 82 in FIG. 8, and are disposed as shown to underlie that portion of the flexible separator piece 32 as is wound around take-up spool 58 immediately to the right of separator piece "edge" 80, thus insuring that any sorbed isolation liquid 52 as may tend to separate and fall from the separator piece beyond "edge" 80 in the counter-clockwise direction as seen in FIG. 8 upon the continued advancement of the separator piece will be effectively prevented from falling into contact with the sample liquid analysis means 68.

System controller 70 is programmed to activate drive motor 60, and thus advance flexible separator piece 32 at a rate carefully predetermined to avoid isolation liquid saturation of the relevant lower portion of the exposed length of the separator piece, thereby insuring that the same remains fully effective to the isolation-blood serum sample liquid separation task at hand for the entire series of the blood serum sample liquid segments of interest. This advance may be continuous, or may be periodic.

As an alternative to the representative application of FIGS. 7 and 8, it will be clear that the liquid separation device 30 may also find use in an application as illustrated by FIGS. 5, 6 and 7 wherein the isolation liquid-encapsulated sample liquids are manually sequentially applied thereto. In such instance, advancement of the flexible separator piece 32 could also be accomplished manually, most probably on a periodic basis as and when determined to be required.

Figure 10:
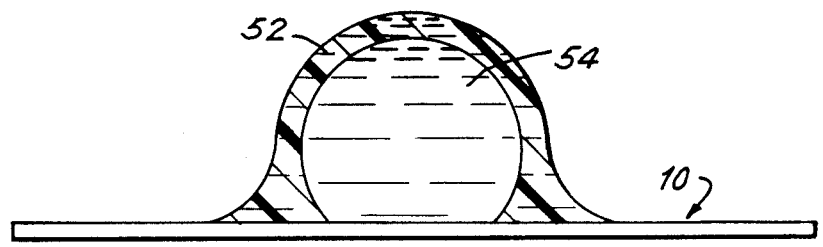
FIGS. 10 and 11 are respectively side elevational views illustrating a third application of the apparatus and method of our invention to the separation of immiscible liquids.
Figure 11:
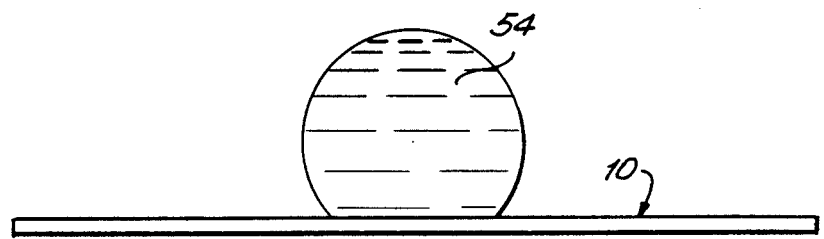

Referring now to FIGS. 10 and 11 of the drawings, the same will be seen to depict an application of the immiscible liquids separator device of our invention, for example, separator device 10 of FIG. 1, wherein the device is maintained essentially level rather than inclined. For such application, the isolation liquid encapsulated aqueous sample liquid globule, as again indicated at 52 and 54 in FIG. 10, is formed and disposed in any applicable manner, again for example by use of the Pipettmen 48 as illustrated and described in some detail hereinabove with regard to FIGS. 5, 6 and 7, upon the upper surface of separator device 10. In this instance, however, the essentially level orientation of the separator device 10 will result in the maintenance of that isolation liquid encapsulated aqueous sample liquid globule on that upper separator device surface; initially essentially as depicted in FIG. 10. Of course, the selective wettability of the super hydrophobic coating 16 on the upper surface of the separator device 10, to the substantial exclusion of the aqueous sample liquid, will as described in some detail hereinabove very quickly result in the isolation liquid 52 being sorbed by that surface coating and effectively separated from the aqueous sample liquid 54, thus leaving the aqueous sample liquid globule substantially separated from the encapsulating isolation liquid and standing alone as such on the super hydrophobic upper surface of the separator device 10 as illustrated in FIG. 11.

With the thusly substantially separated aqueous sample liquid globule 54 disposed as shown in FIG. 11 on the upper surface of the separator device 10, it will be understood by those skilled in this art that the globule may be readily and effectively removed therefrom, at least in substantial part, for example through appropriate manipulation of a Pipettman or like device, for transfer for additional sample liquid processing and or analysis as the case may be. Alternatively, the separator device 10 with the substantially separated sample liquid globule 54 disposed thereon as illustrated in FIG. 11, may be readily transferred as such, either manually or automatically, to an appropriate sample liquid analysis device, not shown, for example a colorimeter, for analysis of the sample liquid globule 54 in situ on the separator device 10.

For use of the super hydrophobic material coated separator device 10 of FIG. 1 for the invention application of FIGS. 10 and 11, a preferred material for the separator device strip 14 would be aluminum which, when surface coated with Vellox, results in a particularly advantageous aqueous sample liquid globule contact angle as high as 150° as set forth hereinabove. Alternatively, the separator devices 18, 24 or 30 of FIGS. 2, 3 and 4 may be utilized for the invention application of FIGS. 10 and 11 by the respective dispositions of the same in essentially level rather than inclined positions, and retention of the substantially separated aqueous sample liquid globule 54 thereon as described in each instance.

Figure 12:
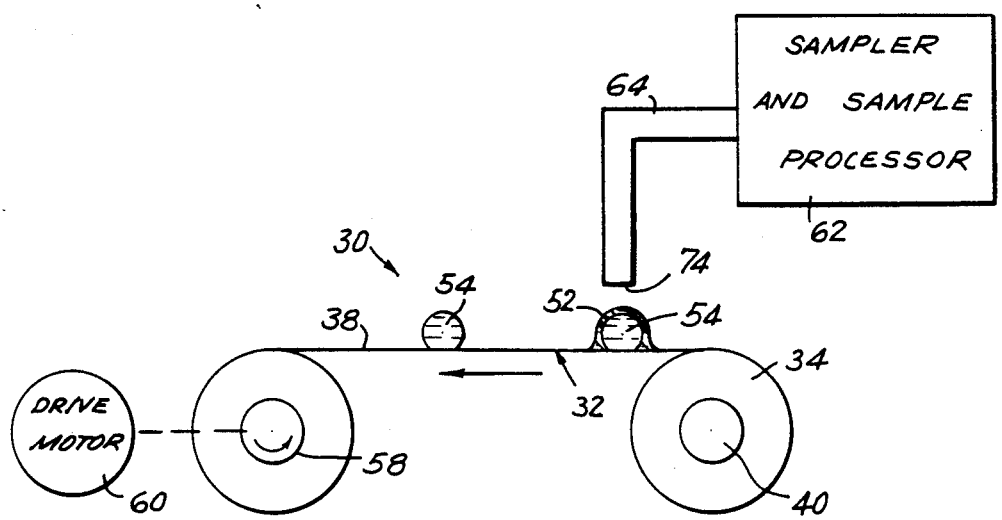
FIGS. 12 and 13 are respectively side elevational views, with certain components depicted schematically, illustrating fourth and fifth applications of the apparatus and method of our invention to the separation of immiscible liquids.

With more specific regard to the use of the separator device 30 of FIG. 4 for this invention application wherein the relevant hydrophobic separator device surface is maintained essentially level, a representative configuration thereof will be seen to be illustrated by FIG. 12, and to include the supply spool 40, take-up spool 58, and drive motor 60 operatively connected to the latter, all in manners described in detail hereinabove with regard to FIG. 8, thereby again providing for advancement of flexible separator piece 32 at a rate carefully predetermined to avoid isolation liquid saturation of the relevant surface of that separator piece. FIG. 12 further includes the representative schematic depiction of sampler and sample processor 62, and sample supply conduit 64, to illustrate the capability of the separator device 30 with the relevant hydrophobic device surface maintained essentially level to receive isolation liquid encapsulated sample liquid globules 52, 54 on an automated feed basis; and also illustrates the substantial separation of the sample liquid globule 52 from the encapsulating isolation liquid globule 54 on the essentially level relevant hydrophobic surface of the separator device 30 as the latter is advanced to the left as seen in FIG. 12.

Figure 13:
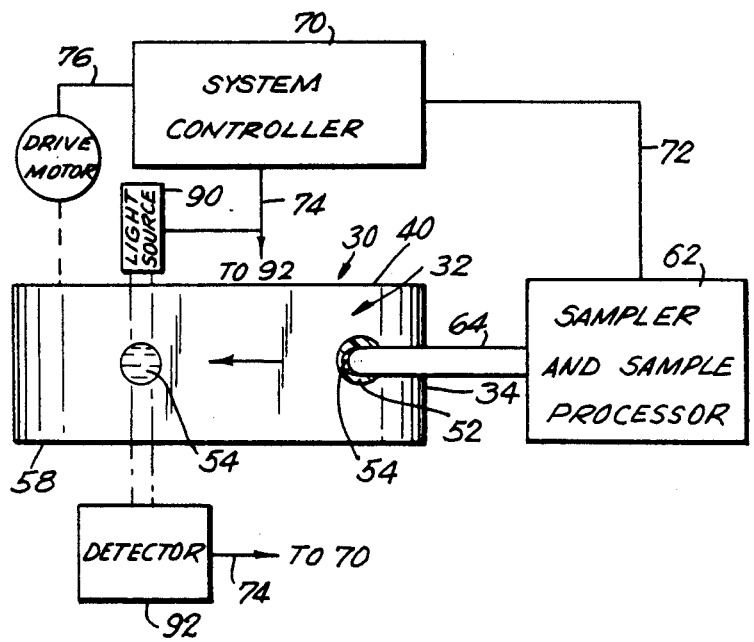

FIG. 13 illustrates a representative application of the separator device 30 of FIG. 12 to an automated sample liquids analysis system; and, in this regard, will be seen to include sampler and sample processor, drive motor, and automated sample liquids analysis device, as respectively schematically indicated at 62, 60 and 68, and a system controller as schematically indicated at 70 and electrically connected to sampler and sample processor 62, drive motor 60 and sample liquids analysis device 68 as indicated by lines 72, 76 and 74 to synchronize and control the respective operations thereof in the manner described in some detail hereinabove with regard to FIG. 8. In this separator device application, the automated sample liquids analysis device may, for example, take the form of a colorimeter; and, to that effect, is illustrated in FIG. 13 as comprising a light source 90 and a photo-detector 92 disposed as shown to opposite sides of the essentially level flexible separator device portion in such manner that the light energy beam from source 90 will pass through the substantially separated sample liquid globules 52 prior to the impingement on the active surface of the photo-detector 92 as those sample liquid globules are advanced in turn with the separator device 30 from the right to the left as seen in FIG. 13. Accordingly, it will be clear to those skilled in this art that highly accurate automated successive sample liquids analyses of the substantially separated sample liquid globules will be advantageously provided by the sample liquids analysis system of FIG. 13, substantially without degradation in that accuracy by the isolation liquid.

Figure 14:
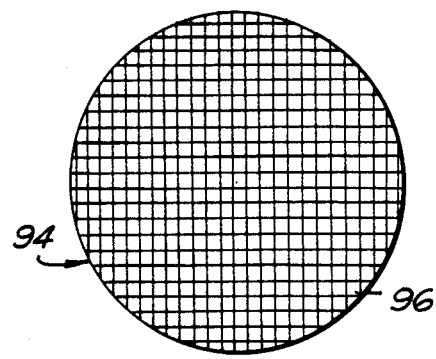
FIG. 14 is a top view of a fifth embodiment of apparatus representatively configured and operable in accordance with the teachings of our invention.

A fifth embodiment of new and improved immiscible liquid separation device representatively configured and operable in accordance with the teachings of our invention is indicated generally at 94 in FIG. 14, and comprises a generally circular separator piece 96 of any appropriately liquid-permeable material, for example a mesh material as illustrated. The mesh material of the separator piece 96 may, for example, take the form of a nylon mesh which is surface coated with Vellox as described hereinabove to render the same super hydrophobic. Alternatively, the mesh material may be Vellox-coated Mylar, aluminum or Teflon, which may or may not be porous, to in any event render the same super hydrophobic; or may take the form of an uncoated, inherently highly, but not super, hydrophobic material such as Teflon which again may or may not be porous. In addition, it will be clear to those skilled in this art that the essential characteristic of liquid permeability for the separator piece 96 can readily be provided by configurations thereof other and different than a mesh, for example a generally circular piece of any of the above mentioned materials with a large plurality of appropriately small diameter holes formed therein, not shown.

Figure 15:
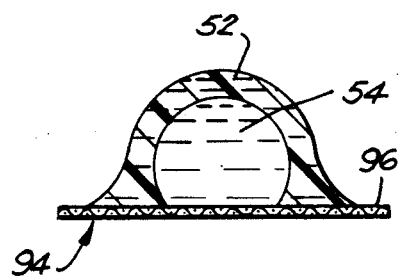
FIGS. 15 and 16 are respectively side elevational views illustrating a sixth application of the apparatus and method of our invention to the separation of immiscible liquids.
Figure 16:
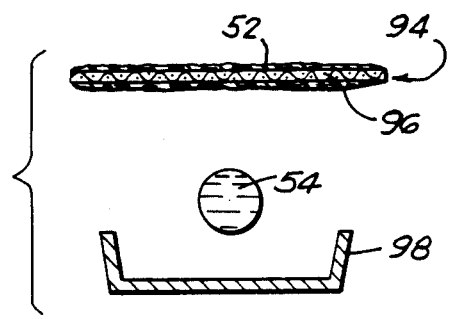

In use of the separator device 94 of FIG. 14, an isolation liquid encapsulated sample liquid globule 52, 54 is placed, as by dropping, generally centrally of the essentially level separator piece 96 as illustrated by FIG. 15. As this occurs, the isolation liquid 52 which selectively wets the hydrophobic mesh material surfaces of the separator piece 96 to the substantial exclusion of the aqueous sample liquid 54, will very quickly be sorbed by those surfaces for substantial retention on and in the liquid-permeable separator piece against the influence of the force of gravity as illustrated by FIG. 16. Concomitantly, and as also illustrated by FIG. 16, the aqueous sample liquid 54 which is substantially excluded as described from the wetting of these hydrophobic mesh material surfaces, will pass very quickly through the liquid-permeable separator piece 96 under the influence of the force of gravity to fall freely therefrom for collection in any appropriate device or instrumentality as indicated schematically at 98 in FIG. 16. Accordingly, substantial separation of the aqueous sample liquid from the isolation liquid is rapidly and effectively accomplished. Although representatively depicted and described as generally circular for conservation of separator piece material in accordance with the generally spherical configuration of the isolation liquid encapsulated sample liquid globule 52, 54, it will be clear that the separator piece 96 may alternatively be of generally rectangular strip-like configuration, and may also be fabricated in the form of a flexible roll.

A representative application of the separator device 94 of FIG. 14 of our invention in combination with a sample liquid reaction device is illustrated in FIGS. 17 and 18, and comprises the disposition and retention, as by a suitable adhesive, of the separator piece 96 in the like-sized sample liquid aperture 100 of a dry chemistry slide 102, again for example the Fuji dry chemistry slide as discussed hereinabove. Although not, per se, forming any part of our invention, it will be understood by those skilled in this art that the dry chemistry slide 102 comprises a housing 104 of any appropriately inert material having the generally rectangular, chemically reactive slide element 106 sandwiched therewithin as best seen in FIG. 18. The sample liquid access aperture 100, and an aligned sample liquid analysis aperture 108 are formed as shown in the housing 104 to respectively extend to opposite sides of the reactive slide element 106, thereby providing access to that element for both sample liquid introduction thereto and sample liquid analysis following appropriate sample liquid-reactive element reaction. Apertures 100 and 108 are generally of $\frac{3}{8}$" diameter.

In use, the isolation liquid encapsulated sample liquid globule, not shown, is placed as by dropping generally centrally of the slide-mounted separator piece 96 in the manner illustrated for the same by FIG. 15. As this occurs, the isolation liquid will be substantially sorbed by the hydrophobic separator piece surfaces and retained thereby substantially out of contact with the chemically reactive slide element 106. Concomitantly, the aqueous sample liquid will pass through the separator piece 96 under the influence of the force of gravity for flow into contact and combination with the reactive element 106 which underlies the separator piece 96. Thus will be clearly understood by those skilled in this art that the essential functions of the substantial separation of the aqueous sample liquid from the isolation liquid and the introduction of the former to the chemically reactive dry chemistry slide element, are effectively combined to significant advantage in accordance with the teachings of our invention.

By all of the above is believed made clear that the new and improved apparatus and method of our invention will function in full accordance with the stated objects thereof to readily, effectively and inexpensively accomplish the virtually immediate and complete separation of immiscible liquids to distinct and spaced locations without contact therebetween.

Although disclosed hereinabove by way of representative examples as applied to the separation of blood serum sample liquids from encapsulating, immiscible isolation liquids attendant blood serum sample liquid analysis, it will be immediately clear to those skilled in this art that the method and apparatus of our invention are by no means limited to such liquids, or to analytical application. In addition, it is not required for satisfactory application of the apparatus and method of our invention that one of the liquids be encapsulated in the other of the liquids. Too, the term "liquid" as used in this specification can, of course, apply to more than one of the same, for example, a liquid mixture.

Various changes may, of course, be made in the herein disclosed embodiments of the apparatus and method of our invention without departing from the spirit and scope thereof as defined in the appended claims.

What is claimed is:

1. In a method for sample liquids analysis wherein successive sample liquids are encapsulated in an immiscible isolation liquid and supplied in turn to liquid separation means for the substantial separation thereof, said isolation liquid being preferentially attractable to and sorbable by a surface to the substantial exclusion of said sample liquids, the improvements wherein the method includes, the steps of, disposing liquid separator means comprising a separator piece of a material which includes said surface relative to an isolation liquid-encapsulated sample liquids supply means to permit flow of said encapsulated sample liquids in turn from said supply means onto said surface, and flowing said isolation liquid-encapsulated sample liquids in turn from said sample liquids supply means onto said surface with said isolation liquid being preferentially attracted to and sorbed by said surface to the substantially separate said sample liquids from said isolation liquid.

2. The method as in claim 1 further comprising, the steps of, analyzing said substantially separated sample liquids in turn substantially free of interference from said isolation liquid.

3. The method as in claim 2 further comprising, the step of, inclining said surface whereby said substantially separated sample liquids will flow therefrom in turn under the influence of the force of gravity for sample liquids analysis remote from said separator piece.

4. The method as in claim 2 further comprising, the step of, maintaining said surface essentially level whereby, said substantially separated sample liquids will be retained thereon for sample liquids analysis.

5. The method as in claim 2 further comprising, the step of, forming said separator piece of a material which is permeable by said sample liquids whereby, said substantially separated sample liquids will flow therethrough and therefrom under the influence of the force of gravity for sample liquids analysis remote from said separator piece.

6. The method as in claim 2 further comprising, the step of, operatively associating sample liquids reaction means with said separator means to receive said substantially separated sample liquids therefrom for reaction therewith and analysis of the thusly reacted sample liquids.

7. A liquid separation apparatus for the separation of first and second immiscible liquids from a common source thereof wherein the first of said liquids is preferentially attractable to and sorbable by a surface to the substantial exclusion of the second of said liquids, wherein the apparatus comprises, liquid separation means comprising a separator piece of a material which includes said surface, said separator piece being impermeable to said first and second liquids, said surface being disposed in such manner relative to said liquids source to permit flow of said liquids from said source onto said surface, and means for inclining said surface relative to a horizontal plane whereby, said first and second liquids may be flowed from said liquids source onto said surface with said first liquid being preferentially attracted to and sorbed by said surface tot he substantial exclusion of said second liquid to thereby substantially separate said first and second liquids on said separator piece. with said substantially separated second liquid flowing from said separator piece under the influence of the force of gravity.

8. The apparatus as in claim 7 further comprising, reaction means operatively associated with said separator piece surface for the flow of said substantially separated second liquid onto said reaction means from said separator piece surface whereby, said substantially separated second liquid may flow from said separator piece surface onto said reaction means for reaction therewith.

9. A liquid separation apparatus for the separation of first and second immiscible liquids from a common source thereof wherein the first of said liquids is preferentially attractable to and sorbable by a surface tot he substantial exclusion of the second of said liquids, wherein the apparatus comprises, liquid separation means comprising a separator piece of a material which includes said surface, said separator piece being impermeable to said first and second liquids, said surface being disposed in such manner relative to said liquids source to permit flow of said liquids from said source onto said surface whereby, said first and second liquids may be flowed from said liquids source onto said surface with said first liquid being preferentially attracted to and sorbed by said surface to the substantial exclusion of said second liquid to thereby substantially separate said first and second liquids on said separator piece, said material being flexible, and said piece of said material taking the form of a roll of said material.

10. The apparatus as in claim 9 further comprising, means operatively associated with said roll of material and operable to unwind the same to progressively expose different portions of said surface to flow of said liquids from said liquids source.

11. A liquid separation apparatus for the separation of first and second immiscible liquids from a common source thereof wherein the first of said liquids is preferentially attractable to and sorbable by a surface to the substantial exclusion of the second of said liquids, wherein the apparatus comprises, liquid separation means comprising a separator piece f a material which includes said surface, said separator piece being impermeable to said first and second liquids, said surface being disposed in such manner relative to said liquids source to permit flow of said liquids from said source onto said surface, said material being porous whereby, said first and second liquids may be flowed from said liquids source onto said surface with said first liquid being preferentially attracted to and sorbed by said surface to the substantial exclusion of said second liquid to thereby substantially separate said first and second liquids on said separator piece.

12. The apparatus as in claim 11 wherein, said surface is formed by a coating on said porous material.

13. The apparatus as in claim 12 wherein said first liquid is hydrophobic, said coating is super-hydrophobic, and said second liquid is aqueous.

14. The apparatus as in claim 11 wherein, said first liquid and said porous material are hydrophobic, and said second liquid is aqueous.

15. A liquid separation method for the separation of first and second immiscible liquids from a common source thereof wherein the first of said liquids is preferentially attractable to and sorbable by a surface to the substantial exclusion of the second of said liquids, wherein the method comprises, the steps of, disposing liquid separator means comprising a separator piece of a material which includes said surface, and which is impermeable to said first and second liquids, relative to said liquids source in such manner as to enable flow of said liquids from said common source onto said surface, inclining said surface relative to a horizontal plane, and flowing said liquids from said source onto said surface whereby, said first liquid will be preferentially attracted to and sorbed by said surface to the substantial exclusion of said second liquid to thereby substantially separate said first and second liquids on said separator piece, and said substantially separated second liquid will flow from said surface under the influence of the force of gravity.

16. In sample liquid analysis apparatus including means to encapsulate successive sample liquids in an immiscible isolation liquid and supply the same in turn to liquid separation means for the substantial separation thereof, said isolation liquid being preferentially attractable to and sorbable by a surface to the substantial exclusion of said sample liquids, the improvements wherein said sample liquid separation means includes a separator piece of a material which includes said surface, said surface being disposed in such manner relative to said encapsulated sample liquids supply means to permit flow of said encapsulated sample liquids in turn from said supply means to said surface, and means for inclining said surface relative to a horizontal plane whereby, said isolation liquid-encapsulated sample liquids may be flowed in turn from said sample liquids supply means onto said surface, with said isolation liquid being preferentially attracted to and sorbed by said surface to the substantial exclusion of said sample liquids to thereby substantially separate said sample liquids from said isolation liquid on said separator piece surface, and said substantially separated sample liquids will flow from said surface under the influence of the force of gravity for sample liquids analysis remote from said separator piece.

17. In a sample liquid analysis apparatus including means to encapsulate successive sample liquids in an immiscible isolation liquid and supply the same in turn to liquid separation means for the substantial separation thereof, said isolation liquid being preferentially attractable to and sorbable by a surface to the substantial exclusion of said sample liquids, the improvements wherein said liquid separation means includes a separator piece of a material which includes said surface, said surface being disposed in such manner relative to said encapsulated sample liquids supply means to permit flow of said encapsulated sample liquids in turn from said supply means onto said surface whereby, said isolation liquid-encapsulated sample liquids may be flowed in turn from said sample liquids supply means onto said surface, with said isolation liquid being preferentially attracted to and sorbed by said surface to the substantial exclusion of said sample liquids to thereby substantially separate said sample liquids from said isolation liquid, said material being permeable by said sample liquids whereby said substantially separated sample liquids will flow therethrough and therefrom under the influence of the force of gravity, said apparatus further comprising sample liquids reaction means for reaction with said substantially separated sample liquids, said sample liquids reaction means being operatively associated with said separator piece and operable to receive said substantially separated sample liquids therefrom in turn for reaction therewith, and sample liquids analysis means operatively associated with said reaction means and operable to analyze said substantially separated and reacted sample liquids in turn substantially free of interference from said isolation liquid.

18. A liquid separation apparatus for the separation of first and second immiscible liquids from a common source thereof wherein the first of said liquids is preferentially attractable to and sorbable by a surface to the substantial exclusion of the second of said liquids, wherein the apparatus comprises, liquid separation means comprising a separator piece of a material which includes said surface, said surface being essentially smooth, said surface being disposed in such manner relative to said liquids source to permit flow of said liquids from said source onto said surface whereby, said first and second liquids may be flowed from said liquids source onto said surface with said first liquid being preferentially attracted to and sorbed by said surface to the substantial exclusion of said second liquid to thereby substantially separate said first and second liquids on said separator piece.

19. In liquid separation apparatus for the separation of first and second liquids from a common source thereof wherein the first of said liquids is preferentially attractable to and sorbable by a surface to the substantial exclusion of the second of said liquids, wherein the apparatus comprises, liquid separation means comprising a separator piece of a material which includes said surface, said surface being essentially unconfined, said surface being disposed in such manner relative to said liquids source to permit flow of said liquids from said source onto said surface whereby, said first and second liquids may be flowed from said liquids source onto said surface with said first liquid being preferentially attracted to and sorbed by said surface to the substantial exclusion of said second liquid to thereby substantially separate said first and second liquids on said separator piece.

20. A liquid separation and reaction apparatus for the separation of immiscible sample and isolation liquids from a common source thereof, and the reaction of the separated sample liquid for analysis, and wherein said isolation liquid is preferentially attractable to and sorbable by a surface to the substantial exclusion of said sample liquid, wherein the apparatus comprises, liquid separation means comprising a separator piece of a material which includes said surface, said material being permeable by said sample liquid, said surface being disposed in such manner relative to said liquids source to permit the flow of said isolation and sample liquids therefrom onto said surface, sample liquid reaction means for reaction with said sample liquid for sample liquid analysis, and mounting means operatively connected to said separator piece and said sample liquid reaction means for mounting said sample liquid reaction means below said separator piece whereby, said isolation and sample liquids may be flowed from said common liquids source onto said separator piece with said isolation liquid being sorbed by said separator piece to substantially separate the same from said sample liquid, and said substantially separated sample liquid flowed from said surface through said separator piece under the influence of he force of gravity onto said sample liquid reaction means for reaction therewith and sample liquid analysis.

21. Apparatus as in claim 20 wherein, said mounting means comprise a housing of a dry chemistry slide, and said sample liquid reaction means comprise a reactive element of said dry chemistry slide.

* * * * *